United States Patent
Ghelli et al.

(10) Patent No.: US 6,723,283 B2
(45) Date of Patent: Apr. 20, 2004

(54) DEVICE FOR OXYGENATING BLOOD IN AN EXTRACORPOREAL CIRCUIT

(75) Inventors: Nicola Ghelli, S. Pietro in Casale (IT); Edgardo Costa Maianti, Mirandola (IT); Ivo Panzani, Mirandola (IT)

(73) Assignee: Dideco S.p.A., Mirandola (IT)

( * ) Notice: Subject to any disclaimer, the term of this patent is extended or adjusted under 35 U.S.C. 154(b) by 262 days.

(21) Appl. No.: 09/920,999

(22) Filed: Aug. 2, 2001

(65) Prior Publication Data

US 2002/0049401 A1 Apr. 25, 2002

(30) Foreign Application Priority Data

Aug. 8, 2000 (IT) ...................................... MI2000A1852

(51) Int. Cl.[7] .......................... A61M 1/36; A61M 37/00; B01D 47/00; C10J 1/10
(52) U.S. Cl. .......................... 422/45; 422/44; 604/6.14; 604/4.01; 261/29; 261/101; 261/DIG. 28; 128/DIG. 3
(58) Field of Search ...................... 422/44–48; 604/6.01, 604/4.01, 6.14; 210/321.6–321.62, 321.64, 348; 128/DIG. 3; 261/1, 2, 5, 6, 158, 19, 20, 24, 28, 29, 75, 100–110, DIG. 28; 435/283.1, 289.1, 297.1–297.2, 294.1

(56) References Cited

U.S. PATENT DOCUMENTS

| | | | | |
|---|---|---|---|---|
| 4,676,771 A | * | 6/1987 | Henke | ........................ 604/6.09 |
| 5,312,479 A | * | 5/1994 | Weinstein et al. | ............. 96/178 |
| 5,582,794 A | * | 12/1996 | Hagiwara et al. | .............. 422/48 |
| 5,632,894 A | * | 5/1997 | White et al. | ................. 210/436 |
| 5,762,869 A | * | 6/1998 | White et al. | ................... 422/48 |
| 5,770,149 A | * | 6/1998 | Raible | ........................... 422/46 |
| 5,782,791 A | * | 7/1998 | Peterson et al. | ............ 604/4.01 |
| 6,451,257 B1 | * | 9/2002 | Flamer | ......................... 422/44 |

\* cited by examiner

*Primary Examiner*—Patricia Bianco
(74) *Attorney, Agent, or Firm*—Popovich, Wiles & O'Connell, P.A.

(57) ABSTRACT

A device for oxygenating blood in an extracorporeal circuit includes a first structure suitable to delimit a portion of space-containing capillaries made of microporous membrane. The capillaries convey oxygen and are wet externally by blood flowing through a portion of space between an intake connector, which is connected to a venous line of the extracorporeal circuit, and a delivery connector. The device includes a second structure monolithically connected and contiguous to the first structure. The second structure is suitable to contain blood filtration means that divide the portion of space delimited thereby into a blood distribution chamber, provided with an air vent and connected to the delivery connector of the first structure, and a blood collection chamber provided with a delivery connector connected to the arterial line of the extracorporeal circuit.

5 Claims, 7 Drawing Sheets

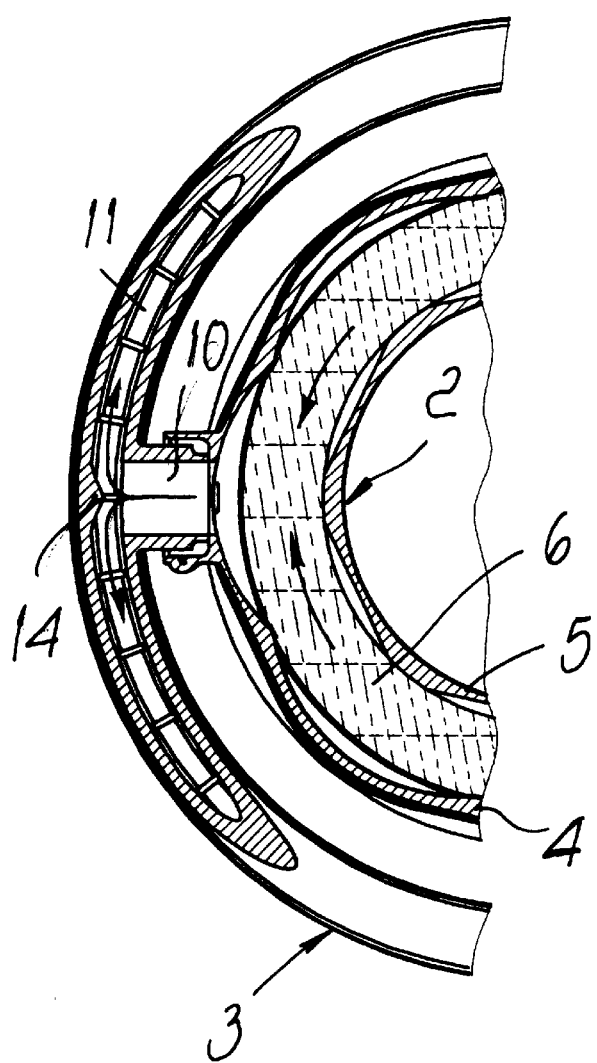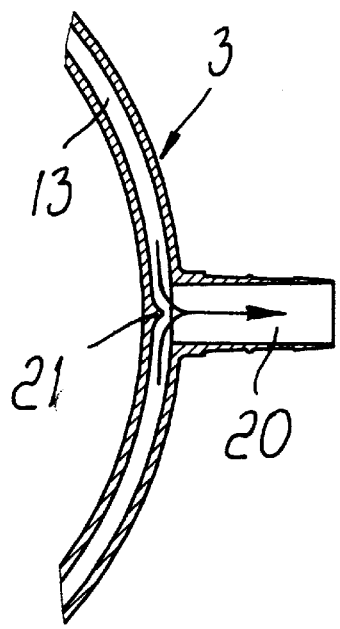

DEVICE FOR OXYGENATING BLOOD IN AN EXTRACORPOREAL CIRCUIT

FIELD OF THE INVENTION

This invention relates to a device for oxygenating blood in an extracorporeal circuit.

BACKGROUND OF THE INVENTION

During surgery, blood flows through extracorporeal circuits. The extracorporeal circuits include an oxygenation device to transfer oxygen to the blood received from the patient by means of a line which is known as venous line and then return it to the patient by means of a line known as arterial line.

The structure of the oxygenator is such as to delimit a portion of space which contains capillaries made of microporous membrane which convey oxygen and are wet externally by the blood that flows through this portion of space. There are also oxygenators which include a heat exchanger through which the blood is meant to flow before entering the oxygenator in order to be kept at the correct temperature.

Often on the arterial line there is a filter (the arterial filter), which is meant to retain any air bubbles present in the blood in order to prevent them from remaining in the blood that returns to the patient. However, this presence can be the source of problems for operators when one considers the inherent complexity of the extracorporeal circuit in which the arterial filter is introduced.

SUMMARY OF THE INVENTION

The aim of the present invention is therefore to provide a blood oxygenation device in which the extracorporeal circuit is simplified and which offers maximum safety in preventing air bubbles from being contained in the blood that returns to the patient.

The proposed aim is achieved by a blood oxygenation device comprising a first structure suitable to delimit a portion of space which contains capillaries made of microporous membrane. The capillaries convey oxygen and are wet externally by blood flowing through the portion of space between an intake connector, which is connected to the venous line of the extracorporeal circuit, and a delivery connector. There is a second structure monolithically connected and contiguous to the first structure suitable to contain blood filtration means which divide the portion of space delimited thereby into a blood distribution chamber, provided with an air vent and connected to the delivery connector of the first structure, and a blood collection chamber which is provided with a delivery connector which is connected to the arterial line of the extracorporeal circuit.

In one aspect, this invention is a device for oxygenating and filtering blood in an extracorporeal circuit comprising a housing defining first and second interior chambers, the first chamber containing a plurality of microporous filters and having a blood inlet and a blood outlet connected to the first chamber to define a blood flow path along an exterior of the hollow fibers and having a gas inlet and a gas outlet connected to the first chamber to define a gas flow path through the lumens of the hollow fibers, the second chamber containing a filtration membrane and having a blood inlet and a blood outlet connected to the second chamber to define a blood flow path through the filtration membrane, the blood inlet of the second chamber being connected to receive blood from the blood outlet of the first chamber.

In a second aspect, this invention is an integrated device for oxygenating and filtering blood in an extracorporeal circuit, comprising an oxygenator having a housing including a top, a bottom, and a side wall together defining an oxygenation chamber containing a microporous membrane, the housing having a blood inlet and a blood outlet positioned to define a blood flow path along a first side of the microporous membrane and a gas inlet and a gas outlet positioned to define a gas flow path along a second side of the microporous membrane; and an arterial blood filter having a housing including a top and bottom, a substantially cylindrical outer wall, and a substantially cylindrical inner wall together defining a substantially ring-shaped interior chamber containing a filtration membrane, the inner wall defining a substantially cylindrical opening in the housing of the arterial filter, the housing having a blood inlet connected to the interior chamber on a first side of the filtration membrane and a blood outlet connected to the interior chamber on a second side of the filtration membrane, to define a blood flow path through the filtration membrane, the blood inlet of the arterial filter being connected to the blood outlet of the oxygenator, the housing of the oxygenator being rigidly connected to the housing of the arterial filter and positioned in the substantially cylindrical opening in the housing of the arterial filter.

In a third aspect, this invention is an integrated device for use in an extracorporeal blood circuit, comprising a housing defining a first portion and a second portion; means for oxygenating blood contained within the first portion of the housing, the oxygenating means including a blood inlet and a blood outlet; and means for filtering oxygenated blood, the filtering means having a blood inlet connected to receive blood from the blood outlet of the oxygenating means and a blood outlet.

In a fourth aspect, this invention is a monolithic device for use in extracorporeal blood circuit, comprising a housing having a blood oxygenator portion and an arterial blood filter portion, the blood oxygenator portion containing a gas exchange membrane and having a blood inlet and a blood outlet defining a blood flow path along a first side of the gas exchange membrane and having a gas inlet and a gas outlet for defining a gas flow path along a second side of the gas exchange membrane, the arterial blood filter portion containing a filtration membrane and having a blood inlet and a blood outlet defining a blood flow path through the filtration membrane, the blood inlet of the arterial blood filter portion being connected to receive blood from the blood outlet of the blood oxygenator portion.

In a fifth aspect, this invention is an arterial blood filter comprising a housing having a top surface, a bottom surface, a substantially cylindrical outer wall and a substantially cylindrical inner wall together defining a substantially ring-shaped interior chamber, the inner wall defining a substantially cylindrical opening from the top surface to the bottom surface of the housing; a filtration membrane contained within the ring-shaped interior chamber; a blood inlet; and a blood outlet, the blood inlet and blood outlet being positioned on the housing to define a blood flow path through the housing across the filtration membrane.

BRIEF DESCRIPTION OF THE DRAWINGS

Further characteristics and advantages will become apparent from the description of a preferred but not exclusive embodiment of the invention, illustrated only by way of non-limiting example in the accompanying drawings, wherein:

FIGS. 4 and 5 are sectional views, taken respectively along the plane IV—IV and along the plane V—V of FIG. 2.

BRIEF DESCRIPTION OF THE PREFERRED EMBODIMENTS

Figure 1:
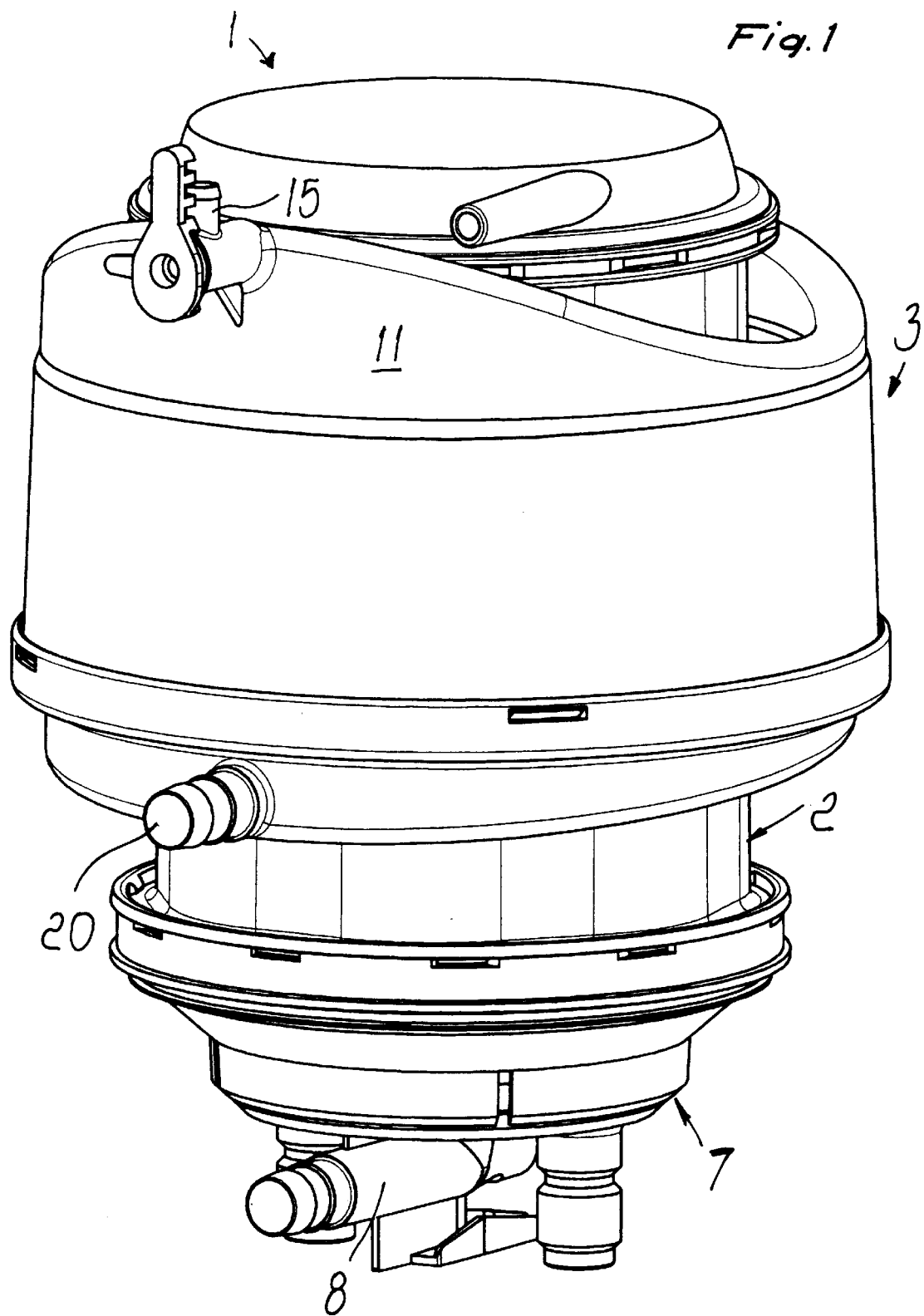
FIG. 1 is a perspective view of the blood oxygenation device of this invention.
Figure 2:
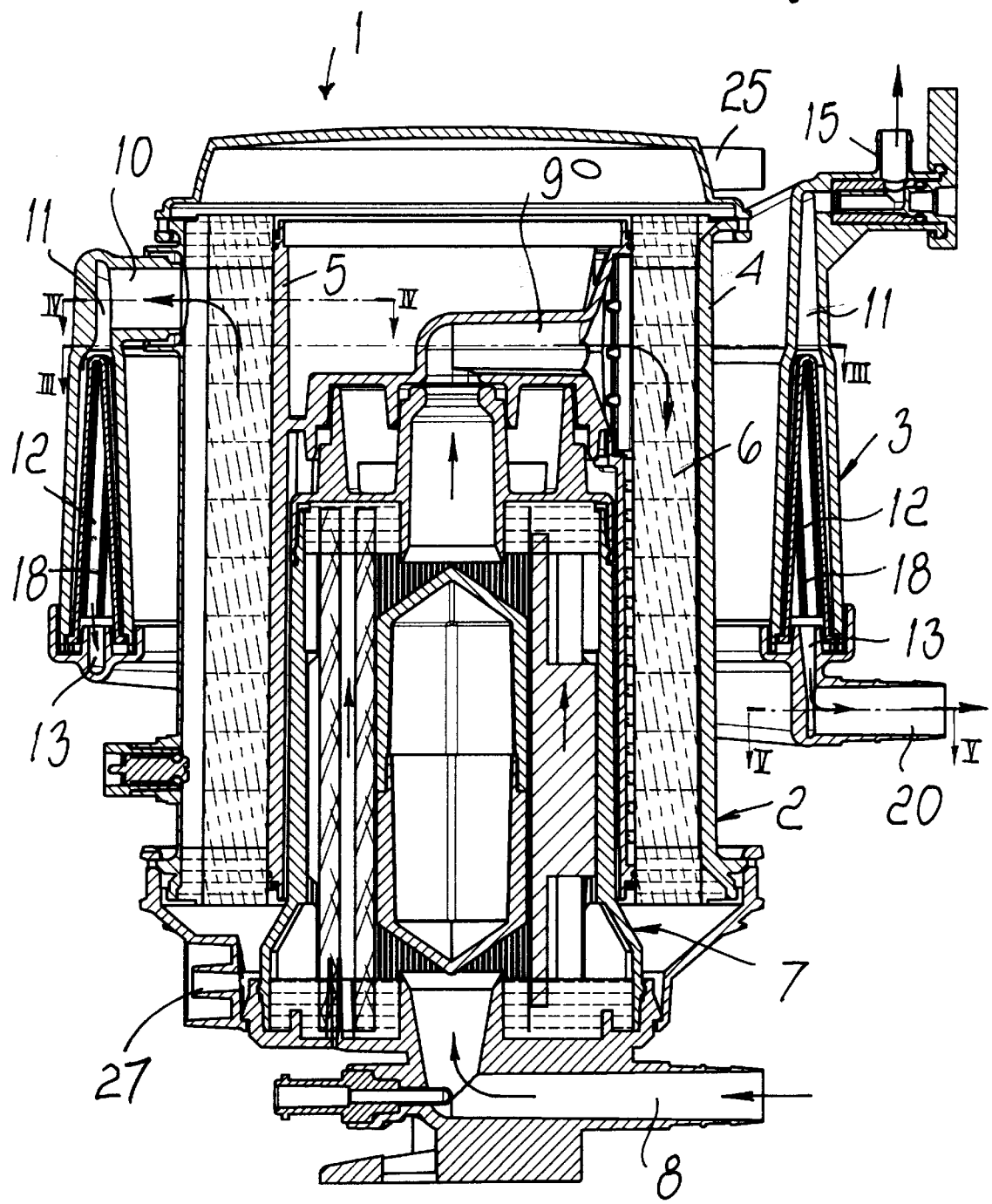
FIG. 2 is a sectional view, along a longitudinal plane, of the device shown in FIG. 1.
Figure 3:
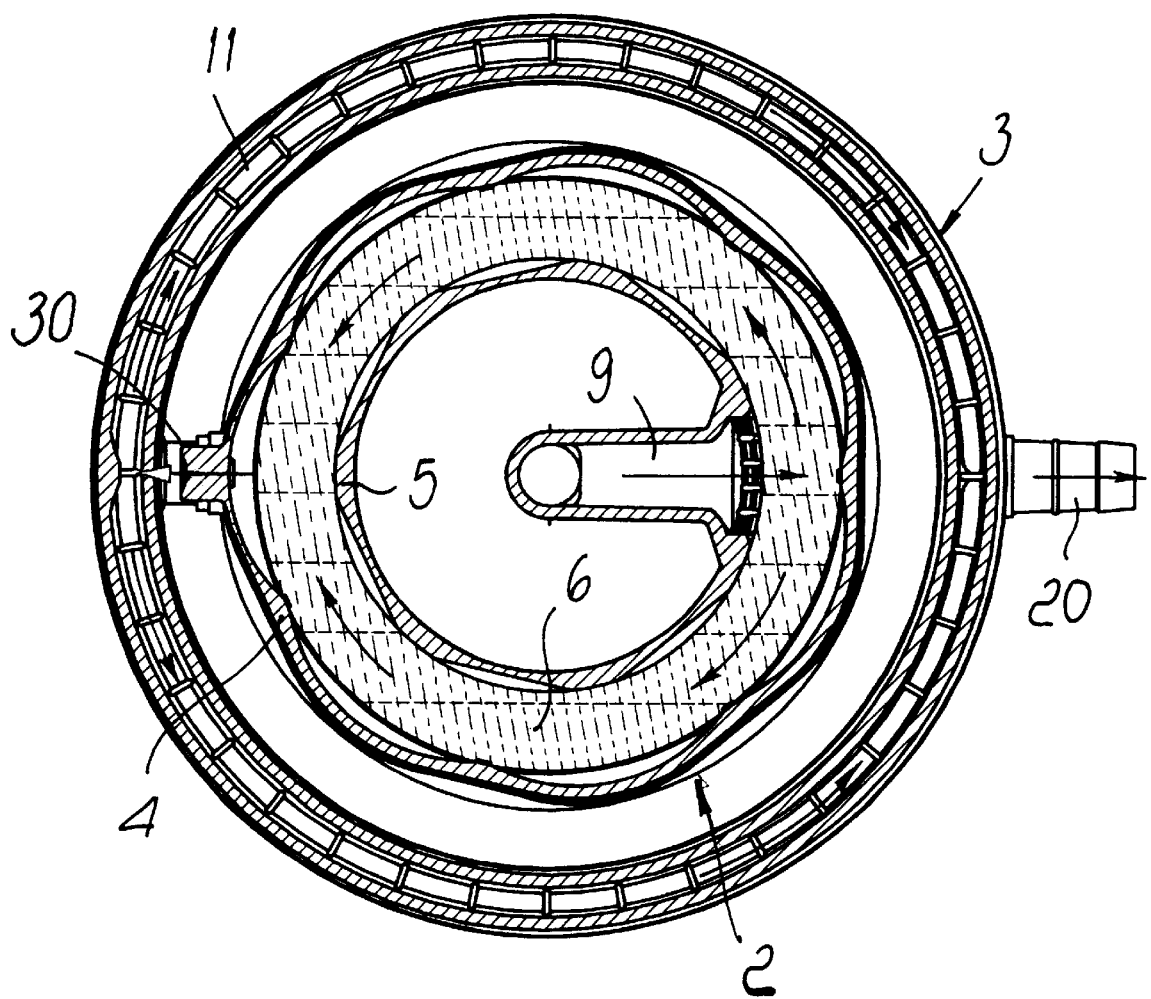
FIG. 3 is a sectional view, taken along the transverse plane III—III of the device shown in FIG. 2.

With reference to the FIGS. 1 to 8, the numeral 1 generally designates the device, which comprises a first structure, generally designated by the reference numeral 2, and a second structure, generally designated by the reference numeral 3, which are monolithically connected.

Structure 2, which constitutes the actual oxygenator, comprises cylindrical walls 4 and 5, which are suitable to define a portion of space 6 comprising an oxygenation chamber that contains in a known manner hollow fibers or capillaries made of microporous membrane which convey oxygen through the lumens of the fibers from gas inlet port 25 to gas outlet port 27. The structure of the oxygenator is similar to that disclosed in commonly assigned U.S. Pat. No. 5,817,278 (Fini et al.), which is incorporated by reference herein in its entirety. Contained within the central portion of the cylindrical oxygenator is a heat exchanger, also known, which is generally designated by reference numeral 7. The inlet to the heat exchanger includes intake connector 8 which is suitable to be connected to the venous line of an extracorporeal circuit.

Blood enters exchanger 7 through inlet 8, flows through it, and reaches the outlet 9 of the heat exchanger. The outlet of the heat exchanger includes connector 9 that leads into a portion of space 6. Blood entering space 6 through connector 9 wets from the outside the capillaries contained therein until the blood arrives, after being oxygenated, at the outlet of the oxygenator. Delivery connector 10 provides a fluid path from the outlet of the oxygenator to the inlet of structure 3. Connector 10 is located in a higher position in order to ensure the elimination of air bubbles, all as shown by the arrows in the figures.

The structure generally designated by reference numeral 3 is monolithically connected to first structure 2 described above and acts as an arterial filter. Structure 3 is annular and comprises housing 30 which defines an internal portion of space which comprises blood distribution chamber 11, intermediate region 12 which comprises filtration means 28, and blood collection chamber 13.

As shown in FIG. 4, blood distribution chamber 11 is connected to connector 10 for receiving the outflow of the blood from the oxygenator at a region which is provided with crest 14 which is suitable to split the blood into two half-ring-shaped flow paths which lie on opposite sides with respect to connector 10 and extend to the diametrically opposite region, where air vent 15 is provided.

Figure 8:
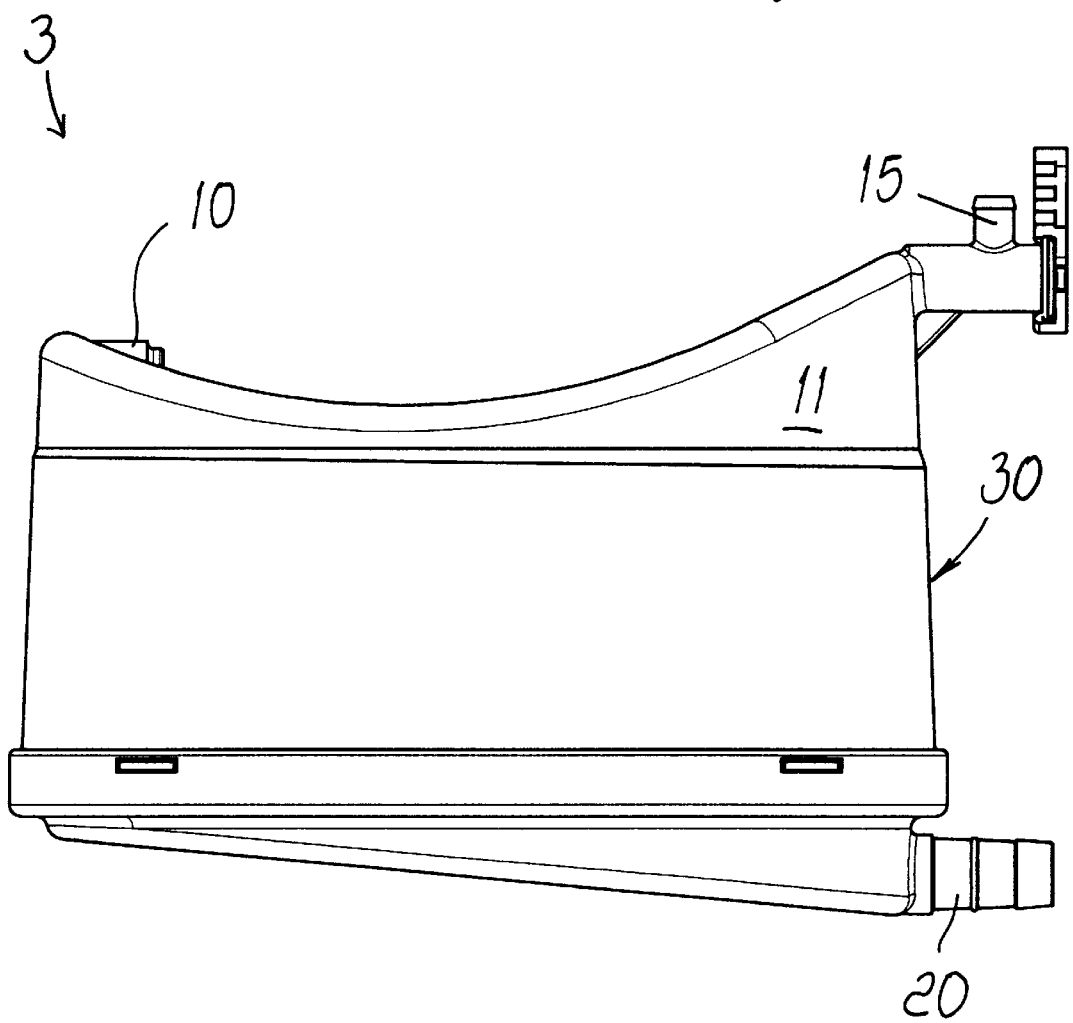
FIG. 8 is a side view of the arterial filter.

The flow path followed by each half-ring, as shown in the figures, is through the internal space defined by the housing of the arterial filter. The housing has a constant base dimension and a height which decreases from the region adjacent connector 10, and then increases to a maximum value at air vent 15 as best seen in FIG. 8. The cross-sectional area of the internal space defining the blood flow passage is a function of the height of the housing. Consequently, the cross-sectional area of the internal space or blood flow passage at the inlet of the arterial filter is greater than that of the cross-sectional area at locations where the height is less than at the inlet.

This leads to a situation in which the blood, after slowing down at the inlet of structure 3, with an initial separation of any air bubbles contained therein, accelerates along a certain extent, facilitating the transport of the bubbles, which thus do not risk remaining trapped in the blood, and finally slows down again proximate to the vent, assuming the best conditions for the final separation of the bubbles, which leave through the vent.

If the amount of air bubbles present in the blood is modest, the described fluid-dynamics treatment can be sufficient to eliminate them completely. If instead the amount is considerable, the filtration membrane completes their elimination from the blood before the blood returns to the patient.

Figure 6:
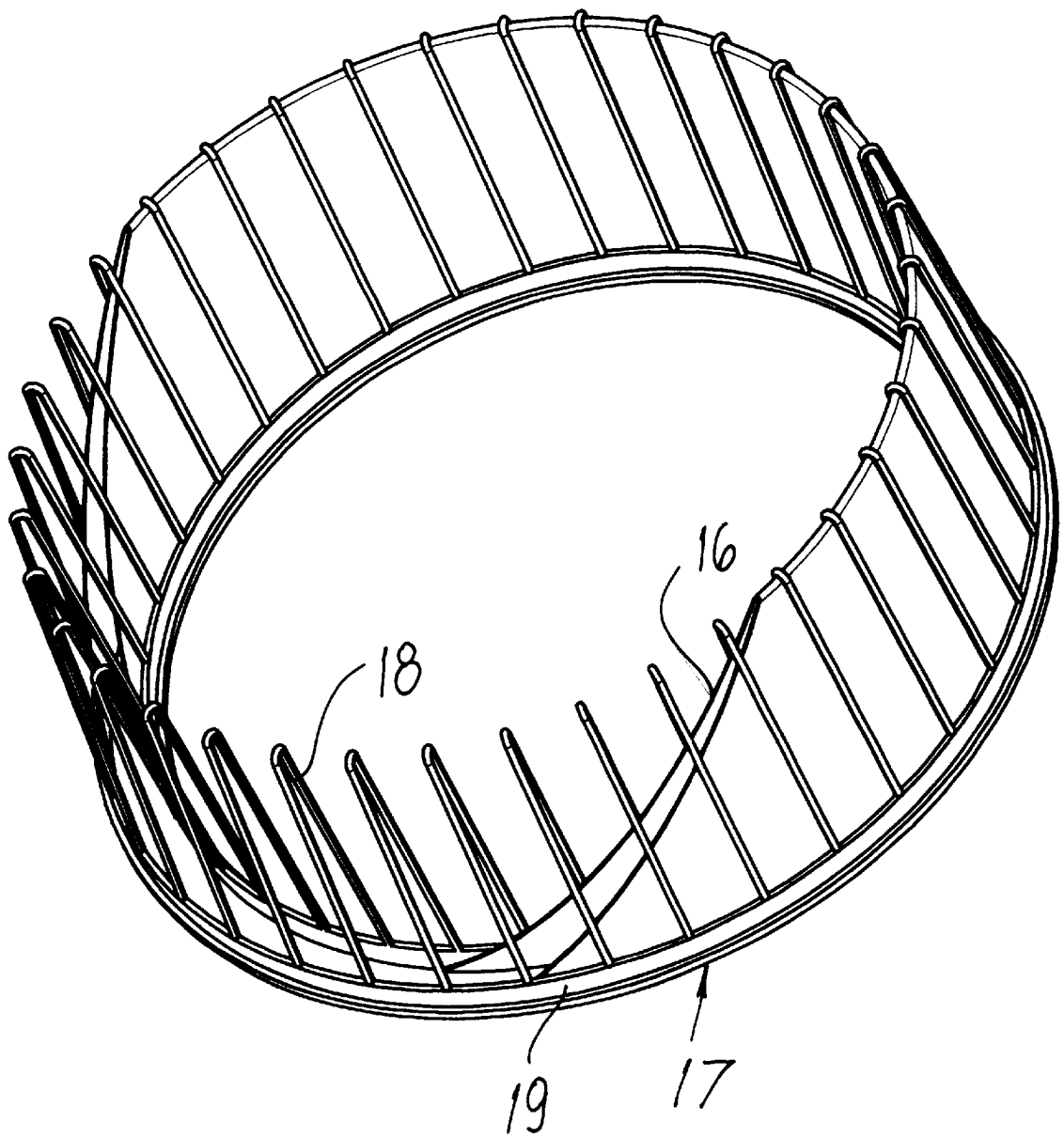
FIG. 6 is a perspective view of the filtration means with a portion of filtration membrane cut away.
Figure 7:
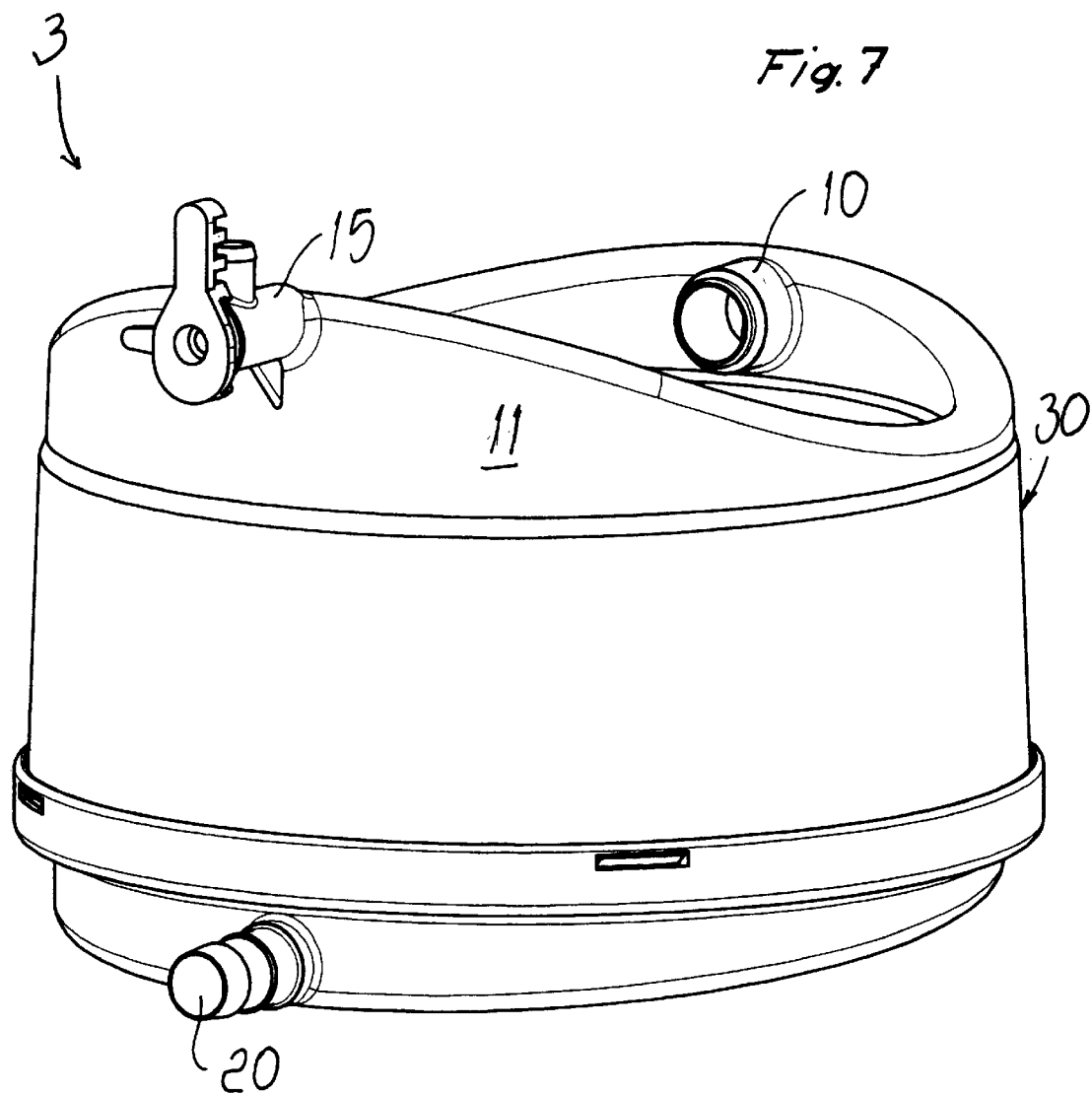
FIG. 7 is a perspective view of the arterial filter.

Blood filtration means 28 contained in region 12 comprises filtration membrane 16, which is supported by annular frame 17. As best seen in FIG. 6, where a portion of the filtration membrane in removed, annular frame 17 comprises wire-like radial U-shaped bridges, such as 18, which extend monolithically from footing 19, which has a constant width. Blood flowing in either half-ring flow path must pass through filtration membrane 16 in order to flow from the inlet to the outlet of the arterial filter.

The blood, after passing through filtration means 28, passes into lower collection chamber 13, (FIG. 5) which is provided with outlet port 20 which is suitable to be connected to the arterial line of the extracorporeal circuit. The lower collection chamber has a constant width and a height which gradually increases from the inlet side of the arterial filter (at connector 10) to the outlet side of the arterial filter (at outlet port 20), to which the blood flow is directed by crest 21.

The described invention is susceptible of numerous modifications and variations, all of which are within the scope of the inventive concept. Thus, for example, the actual oxygenator, which in the described embodiment replicates the content of U.S. Pat. No. 5,817,278 (Fini et al.), may be of any kind, including oxygenators having microporous hollow fiber bundles of various constructions, flat sheet microporous membranes, semi-permeable membranes, and other configurations and structures as known in the art.

What is claimed is:

1. An integrated device for oxygenating and filtering blood in an extracorporeal circuit, comprising:

an oxygenator having a housing including a top, a bottom, and a side wall together defining an oxygenation chamber containing a microporous membrane, the housing having a blood inlet and a blood outlet positioned to define a blood flow path along a first side of the microporous membrane and a gas inlet and a gas outlet positioned to define a gas flow path along a second side of the microporous membrane; and an arterial blood filter having a housing including a top and bottom, a substantially cylindrical outer wall, and a substantially cylindrical inner wall together defining a substantially ring-shaped interior chamber containing a filtration membrane, the inner wall defining a substantially cylindrical opening in the housing of the arterial filter, the housing having a blood inlet connected to the interior chamber on a first side of the filtration membrane and a blood outlet connected to the interior chamber on a second side of the filtration membrane, to define a blood flow path through the filtration membrane, the blood inlet of the arterial filter being connected to the blood outlet of the oxygenator, the housing of the oxygenator being rigidly connected to the housing of the arterial filter and positioned in the substantially cylindrical opening in the housing of the arterial filter.

2. An arterial blood filter comprising:

a housing having a top surface, a bottom surface, a substantially cylindrical outer wall and a substantially cylindrical inner wall together defining a substantially ring-shaped interior chamber, the inner wall defining a substantially cylindrical opening from the top surface to the bottom surface of the housing;

a filtration membrane contained within the ring-shaped interior chamber;

a blood inlet; and a blood outlet, the blood inlet and blood outlet being positioned on the housing to define a blood flow path through the housing across the filtration membrane.

3. A device for oxygenating and filtering blood in an extracorporeal circuit comprising:

a housing defining first and second interior chambers, the first chamber containing a plurality of hollow fibers and having a blood inlet and a blood outlet connected to the first chamber to define a blood flow path along an exterior of the hollow fibers and having a gas inlet and a gas outlet connected to the first chamber to define a gas flow path through lumens of the hollow fibers, the second chamber having a substantially cylindrical outer wall, and a substantially cylindrical inner wall together defining a substantially ring-shaped interior chamber containing a filtration membrane and having a blood inlet and a blood outlet connected to the second chamber to define a blood flow path through the filtration membrane, the blood inlet of the second chamber being connected to receive blood from the blood outlet of the first chamber, the first chamber being rigidly connected to the second chamber and positioned in the substantially cylindrical opening in the second chamber housing.

4. An integrated device for use in an extracorporeal blood circuit, comprising:

a housing defining a first portion and a second portion;

means for oxygenating blood contained within the first portion of the housing, the oxygenating means including a blood inlet and a blood outlet; and means for filtering oxygenated blood contained within the second portion of the housing, the second portion of the housing including a substantially cylindrical outer wall, and a substantially cylindrical inner wall together defining a substantially ring-shaped interior chamber containing a filtration membrane, the filtering means having a blood inlet connected to receive blood from the blood outlet of the oxygenating means and a blood outlet;

the first portion of the housing being rigidly connected to the second portion of the housing and positioned in the substantially cylindrical opening in the second onion of the housing.

5. A monolithic device for use in an extracorporeal blood circuit, comprising:

a housing having a blood oxygenator portion and an arterial blood filter portion;

the blood oxygenator portion containing a gas exchange membrane and having a blood inlet and a blood outlet defining a blood flow path along a first side of the gas exchange membrane and having a gas inlet and a gas outlet for defining a gas flow path along a second side of the gas exchange membrane;

the arterial blood filter portion having a filter housing including a top and bottom, a substantially cylindrical outer wall, and a substantially cylindrical inner wall together defining a substantially ring-shaped interior chamber, the chamber containing a filtration membrane and having a blood inlet and a blood outlet defining a blood flow path through the filtration membrane; and the blood inlet of the arterial blood filter portion being connected to receive blood from the blood outlet of the blood oxygenator portion, the blood oxygenator portion being rigidly connected to the filter housing and positioned in the substantially cylindrical opening in the filter housing.

* * * * *